United States Patent [19]
Ben-Ziony et al.

[11] Patent Number: 6,110,971
[45] Date of Patent: Aug. 29, 2000

[54] FUNGICIDE COMPOSITION COMPRISING A BENZOYLPHENYLUREA

[75] Inventors: Yair Ben-Ziony; Boaz Arzi, both of Kiryat Tivon, Israel

[73] Assignee: Novartis Animal Health US, Inc., Greensboro, N.C.

[21] Appl. No.: 09/244,013

[22] Filed: Feb. 4, 1999

[30] Foreign Application Priority Data

Mar. 2, 1998 [IL] Israel ........................................ 123517
Apr. 16, 1998 [IL] Israel ........................................ 124128

[51] Int. Cl.[7] .......................... A01N 47/34; A61K 31/17; C07C 127/22
[52] U.S. Cl. ............................................... 514/594; 564/44
[58] Field of Search ................................ 514/594; 564/44

[56] References Cited

U.S. PATENT DOCUMENTS 4,798,837  1/1989  Drabek et al. ........................... 514/594
5,837,734  11/1998  Bartsch et al. ........................... 514/594

FOREIGN PATENT DOCUMENTS

97/06687  2/1997  WIPO .
97/36485  10/1997  WIPO .
98/34481  8/1998  WIPO .

OTHER PUBLICATIONS

Sundlof, Stephen F. "Oral dosage form new animal drugs; lufenuron tablets", Federal Register, 62(58): 14301, Mar. 1997.
Sundlof, Stephen F. "Oral dosage form new animal drugs; lufenuron tablet", Federal Register, 62(50): 12085, Mar. 1997.
FDA, "Oral dosage form new animal drugs; lufenuron suspension and tablets", Federal Register, 62(37): 8371, Feb. 1997.
Franc et al., "Use of injectable lufenuron for treatment of infestations of *Ctenocephalides felis* in cats", Am. J. Vet. Res., vol. 58(2): 140–142, 1997.
FDA, "Oral dosage form new animal drugs; lufenuron suspension", Federal Register, 60(80): 20402, Apr. 1995.
FDA, "Oral dosage form new animal drugs; lufenuron tablets", Federal Register, 60(2, Bk. 1); 362, Jan. 1995.
Hink et al., "Evaluation of a single oral dose of lufenuron to control flea infestations", Am. J. Vet. Res., 55(6): 822–824, 1994.
Aets et al., "Side–effects of pesticides on the development of the entomopahtogenic fungus *Paecilomyces fumosoroseus* (Wize) Brown and Smith, strain Apopka 97", Meded.—Fac. Landbouwkd. Toegepaste Bio. Wet. (Univ. Gent), 62(2b): 581–587, 1997.

*Primary Examiner*—Howard C. Lee
*Attorney, Agent, or Firm*—Michael P. Morris

[57] ABSTRACT

The present invention provides a pharmaceutical or veterinary composition comprising, a carrier and an active ingredient being a compound of the following formula I:

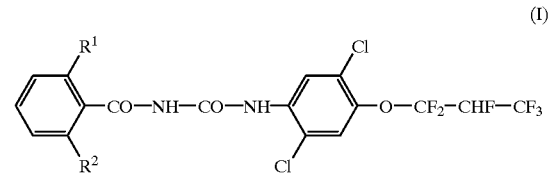

wherein $R^1$ and $R^2$ are each independently hydrogen, halogen or methoxy, as well as salts of the compound of formula I.

Further provided by the invention is a method of treatment of fungal infection, comprising administering to a patient in need, an effective amount of the compound of said formula I.

10 Claims, No Drawings

FUNGICIDE COMPOSITION COMPRISING A BENZOYLPHENYLUREA

FIELD OF THE INVENTION

The present invention relates to a new use of benzoylphenylureas derivatives. More particularly, the present invention relates to benzoylphenylureas derivatives for use in combating fungal infections.

BACKGROUND OF THE INVENTION

Fungi are causative agents of various superficial skin lesions. The fungi live on the surface of the skin and use keratin as major solutions of nutrients. Fungi are found on various skin regions including in the legs, in the genital area, below the nails, etc. In addition, occasionally, particularly in individuals with an immune deprivation, fungi can develop on various other tissues such as on the oral mucosa. Furthermore, there are occasional fungi infections which may be systemic.

The fungi cells are typically surrounded by cell walls that contain complex polysaccharides, primarily chitin, chitosan, glucans and mannans.

U.S. Pat. No. 4,798,837, discloses N-benzoyl-N'-2,5-dichloro-4-hexafluoropropyloxy-phenylureas which were found to be effective as a pesticide, particularly for controlling insects of the order Acarina. One of these compounds, known by the generic name Lufenuron, has found use in veterinary medicine in the control of fleas (sold under the trademark PROGRAM™, by Novartis, Switzerland (this compound has the trivial namne N-[2,5-dichloro-4-(1,1,2,3,3,3-hexafluoropropoxy)-phenylaminocarbonyl]-2,6-difluorobenzamide). Lufenuron in the form of a pill or suspension is given to animals orally in order to prevent infestation of animals by fleas. The therapeutic regime for the use of this drug is typically one administration for several weeks.

GENERAL DESCRIPTION OF THE INVENTION

In accordance with the invention it was found that Lufenuron administration is effective in combating and controlling fungal infection, especially such caused by dermatophytes.

Thus, the present invention provides, by a first of its aspects, a pharmaceutical or veterinary composition comprising, a carrier and an active ingredient being a compound of the following formula I:

(I)

wherein $R^1$ and $R^2$ are each independently hydrogen, halogen or methoxy, as well as salts of the compound of formula I.

Also provided by the present invention is use of a compound of said formula I, for the preparation of a pharmaceutical or veterinary composition for the treatment of fungal infections.

Further provided by the invention is a method of treatment of fungal infection, comprising administering to a patient in need, an effective amount of the compound of said formula I.

Preferred compounds of formula I are those wherein $R^1$ and $R^2$ are each independently fluorine, chlorine or methoxy, particularly such wherein both $R^1$ and $R^2$ are the same. The most preferred compound, according to formula I, is Lufenuron (wherein both $R^1$ and $R^2$ are fluorine).

The salts of the compound of formula I may be salts with a cation of an organic base. Examples of a cation of an organic base, are the following:

$(CH_3)_4N^+$, $(C_2H_5)_4N^+$, $(n-C_3H_7)_4N^+$, $(i-C_3H_7)_4N^+$, $(n-C_4H_9)_4N^\oplus$, $(C_4H_9)_3N^+H$, , and $[CH_3\text{-}(CH_2)_n]_3\text{-}N^+\text{-}CH_3$, wherein n, in the last formula is an integer from 8 to 12.

The carrier, should be a physiologically tolerated carrier, compatible with the compound of formula I or salts. Examples of carriers are various liquids or solids as known per se, e.g. those described in U.S. Pat. No. 4,798,837, the contents of which is incorporated herein by reference.

The compound of formula I may be formulated for oral, parenteral or topical application. Formulating of the compound of formula I for oral or parenteral application, so as to act systemically, is preferred, with oral formulation being particularly preferred.

The term "effective amount" should be understood as meaning an amount effective in achieving a therapeutic effect which may be manifested either in a permanent or temporary improvement in the subject's condition, or in reduction of a fungal infection load. The effective amount may depend, inter alia, on the therapeutic regiment, the type of infection being treated, namely whether it is systemic, topical, etc., on the type of subject treated, i.e. whether it is human or a non human animal, as well as the type of animal, on the age of the subject, etc.

The pharmaceutical or veterinary composition of the invention may, for example be provided in the form of a powder, lyophilizate, etc., for mixing with a physiological solution, e.g. saline for the purpose of parenteral administration. By a further example, the pharmaceutical solution of the invention may be formulated as an oral dosage form, e.g. in the form of a pill or a capsule. In addition, for some applications, the pharmaceutical composition of the invention may also be formulated in the form of a liquid solution intended for oral administration. Furthermore, the composition of the invention may also be formulated for topical administration.

The invention allows a therapeutic treatment of a variety of fungal infections. These may include systemic infections as well as topical fungal infections. In particular, and by a preferred embodiment, the present invention allows treatment of skin fungal infections in both humans and animals, nail or genital fungal infections in humans, eye fungal infections or ear fungal infections in both humans and animals, and others. Particular examples of fungal infections which may be treated in accordance with the invention are caused by dermatophytes such as those of the genus Microsporum (e.g. Microsporum Canis) which cause various skin fungal infections of the skin, nails or hair; those of the genus Aspergillas, and yeasts, e.g. Malassezia or Candida.

The invention can be applied for the treatment of animals, including, but not limited to dogs, cats, cows, sheep, pigs, poultry and others.

The invention will now be illustrated by the following non-limiting examples.

EXAMPLE 1

4,269 animals, including 2,914 dogs and 1,355 cats, which visited a veterinary clinic, were monitored for the occurrence of a fungal infection.

62 dogs, constituting 2.13% of all the monitored dogs, had, on a first visit, an occurrence of a skin fungal infection. 54 cats, constituting 3.9% out of all the monitored cats, had, on a first visit, an occurrence of a skin fungal infection.

429 dogs (14.7% out of all monitored dogs) and 102 cats (7.5% of all monitored cats) received Lufenuron, in order to prevent skin fleas infestation.

All animals were tested for the occurrence of a fungal infection in a subsequent visit to the clinic. In all Lufenuron-treated cats or dogs, none showed signs of fungal infections. In all cases where there was an initial fungal infection (seen at a first visit), it disappeared.

There was only one case of a dog which received a monthly treatment of Lufenuron and it became infected during the treatment with the fungus Asperagilus SP. After the dosage of Lufenuron was doubled, the dog recovered from the fungal infection within fourteen days.

The animals which were treated with Lufenuron were also monitored for the occurrence of a yeast (Candida or Malassegia) infection and none were observed in all treated animals.

EXAMPLE 2

A female dog weighing 3.7 kg, was examined and was found to have a round alopecia in its left leg which glowed under UV radiation. Given these parameters, the infection was diagnosed as microsporum canice, which was later confirmed by laboratory testing.

The dog was treated with two pills of small Program™ pills (each containing 67.8 mg Lufenuron), one tablet every two weeks. Within fourteen days from the onset of the treatment all signs of fungal infection disappeared.

EXAMPLE 3

A male dog weighing about 4 kg, was diagnosed as having an infection of microsporum canice, similarly as in Example 2. The dog was first treated systemically with Griseofulvin and topically with Cyclopiroxsolamine 1%, with no marked effect.

The dog was then treated with Program (1 small tablet) and after ten days signs of healing and hair growth at the site of fungal infection was seen.

EXAMPLE 4

A dog weighing about 5 kg, was diagnosed as having a Trichophyton infection in its right hind leg. Treatment was similarly as in Example 1. Within ten days of the onset of the treatment, hair growth at the site of infection was observed.

EXAMPLE 5

A male dog weighing about 20 kg, had a symmetric alopecia infection, which glowed under UV light, and which was thus diagnosed as being a Microsporum canis infection. This diagnosis was later confirmed by a laboratory testing.

The dog was treated with a large pill of Program™ (containing 409.8 mg of Lufenuron) once every two weeks. After ten days, even prior to administration of the second tablet, the infected skin showed a sign of complete recovery and hair growth.

EXAMPLE 6

A female dog weighing about 40 kg, was diagnosed as having microsporum canice infection similarly as in Example 2. The dog was treated with one large pill of Program (containing 409.8 mg Lufenuron), and another pill given after two weeks. The animal showed signs of recovery within ten days evidenced by growth of hair at the site of infection.

EXAMPLE 7

5 cats living together in the same household, were diagnosed as having Trichophyton infection at various sites over their body. The cats were treated with Program™ suspension (dose). There was a complete recovery in all cases within ten days, evidenced by hair growth in all infection sites.

EXAMPLE 8

6 cats were diagnosed as having Microsporum canis infection. This diagnosis was confirmed by laboratory testing. The cats were treated with injectable Lufenuron at a dose of 20 mg/kg BW in a single injection. Within 8–11 days of the onset of the treatment, the animals showed recovery, evidenced by growth of hair at the site of infection and lack of growing culture in D.T.M. plates.

We claim:

1. A method for the treatment of fungal infection, comprising administering to a patient in need of such treatment, an effective amount of the compound of the following formula I:

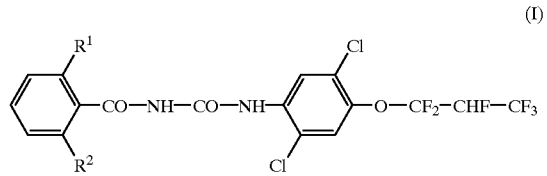

wherein $R^1$ and $R^2$ are each independently hydrogen halogen or methoxy, as well as salts of the compound of formula I.

2. A method according to claim 1, wherein $R^1$ and $R^2$ are each independently fluorine, chlorine or methoxy.

3. A method according to claim 1, wherein $R^1$ and $R^2$ are the same.

4. A method according to claim 3, wherein $R^1$ and $R^2$ are fluorine.

5. A method according to claim 1, comprising oral administration of said compound of formula I.

6. A method according to claim 1, comprising parenteral administration of said compound of formula I.

7. A method according to claim 1, for treating systemic fungal infections.

8. A method according to claim 1, for treating topical fungal infections.

9. A method according to claim 8, wherein the topical fungal infection is caused by a dermatophyte.

10. A method according to claim 1, wherein the fungal infection is caused by a fungus selected from the group consisting of Microsporum, Trichophyton, Aspergillus and yeasts.

* * * * *